United States Patent
Nagaoka et al.

(10) Patent No.: US 6,490,337 B1
(45) Date of Patent: Dec. 3, 2002

(54) X-RAY CT APPARATUS

(75) Inventors: Takayuki Nagaoka, Sakura; Osamu Miyazaki, Ibaraki, both of (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/823,461

(22) Filed: Mar. 30, 2001

(30) Foreign Application Priority Data

Apr. 3, 2000 (JP) ......................................... 2000-100501

(51) Int. Cl.⁷ .................................................. A61B 6/00
(52) U.S. Cl. .............................. 378/20; 378/16; 378/18
(58) Field of Search .............................. 378/4, 16, 18, 378/20

(56) References Cited

U.S. PATENT DOCUMENTS

| 5,450,462 A | * | 9/1995 | Toki et al. ..................... 378/16 |
| 5,696,807 A | * | 12/1997 | Hsieh .......................... 378/109 |
| 5,867,555 A |   | 2/1999 | Popescu et al. ................ 378/16 |
| 6,067,341 A | * | 5/2000 | Horiuchi ........................ 378/8 |
| 6,072,851 A | * | 6/2000 | Sivers ......................... 378/15 |

FOREIGN PATENT DOCUMENTS

JP    5305077    11/1993

* cited by examiner

*Primary Examiner*—David P. Porta
*Assistant Examiner*—Therese Barber
(74) *Attorney, Agent, or Firm*—Cooper & Dunham LLP

(57) ABSTRACT

Before a CT scan for a patient, a model that shows transmission lengths of the patient at rotation angles of an X-ray source is stored in a memory. At the CT scan, X-ray tube currents are controlled according to the transmission lengths at the rotation angles in order to apply X-rays to the patient. The three-dimensional model is homogenous and its material is similar to that of the patient's body, and transmission lengths of the three-dimensional model are converted into those of the patient. The model is acquired by a scannography in a single direction or a CT helical scanning with a small X-ray dose. This reduces the X-ray dose applied to the patient.

24 Claims, 10 Drawing Sheets

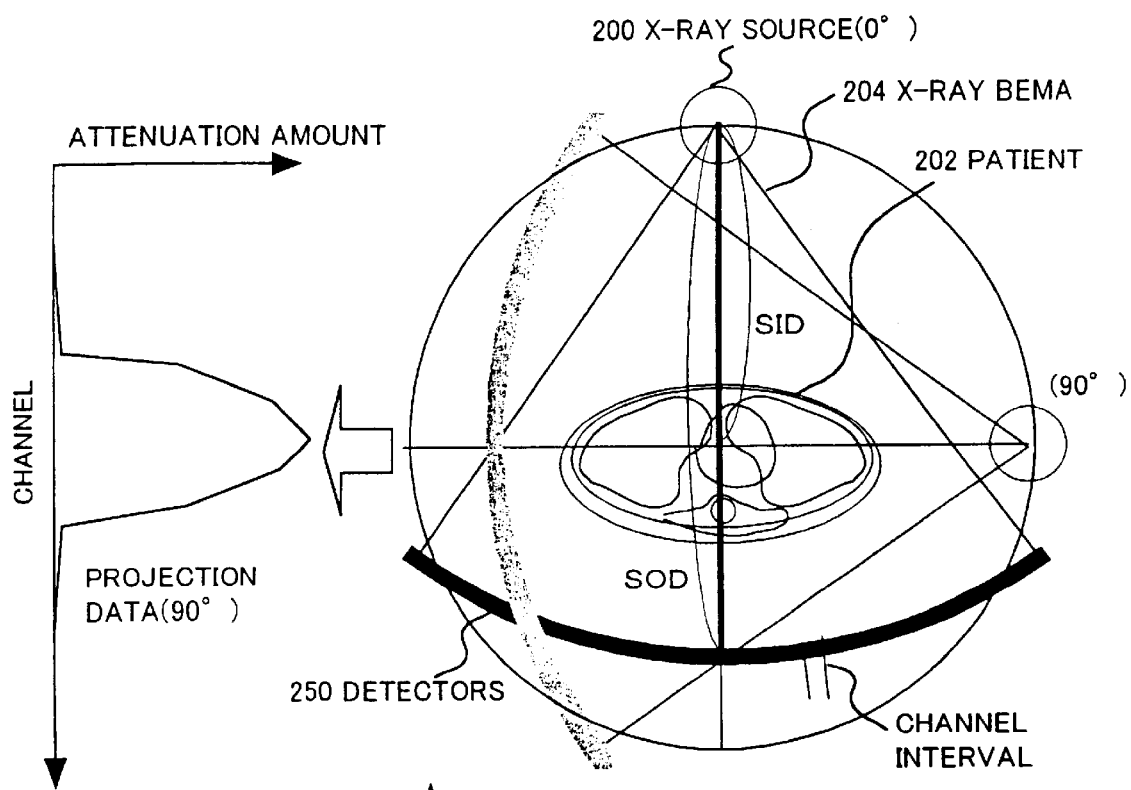
Fig. 3(a)
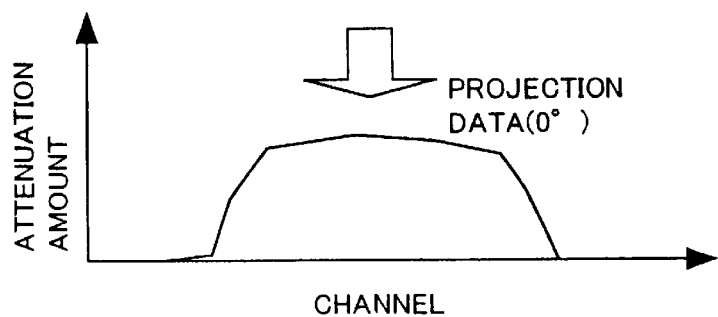
Fig. 3(b)
Fig. 3(c)

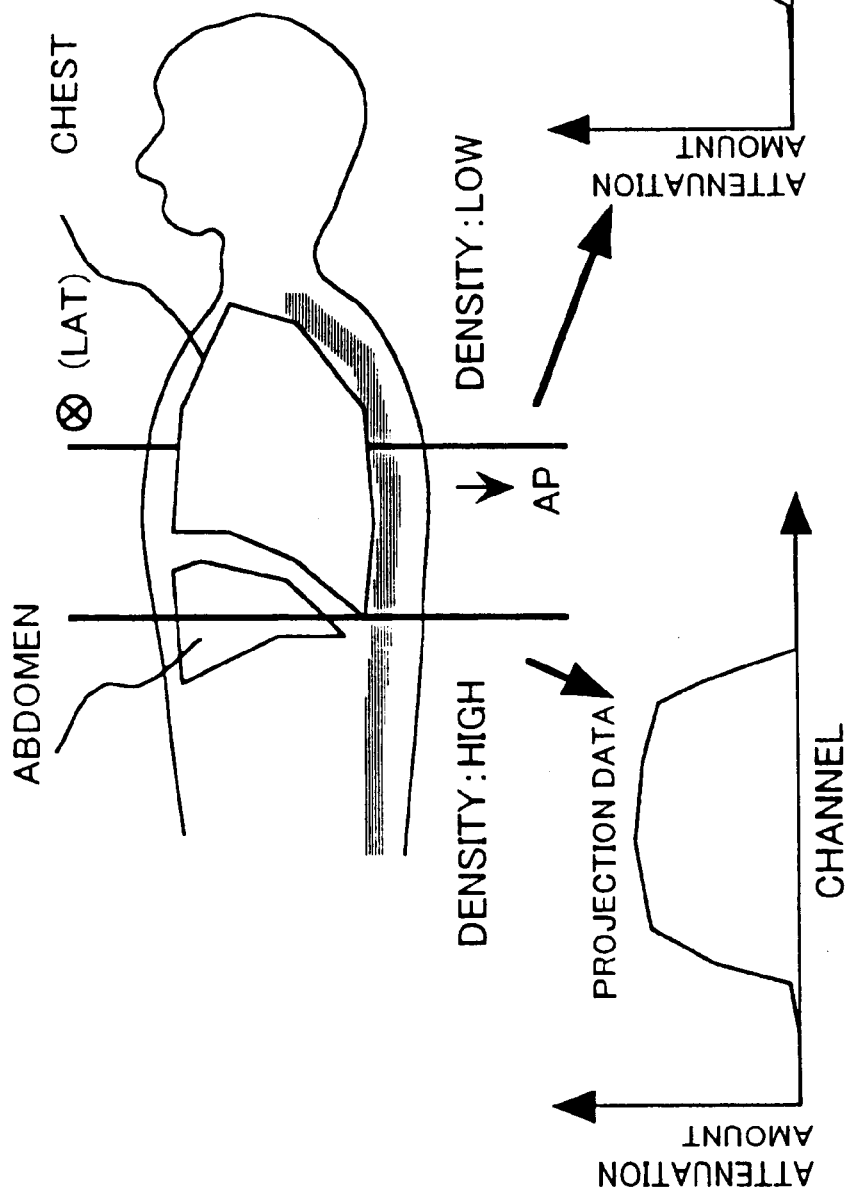

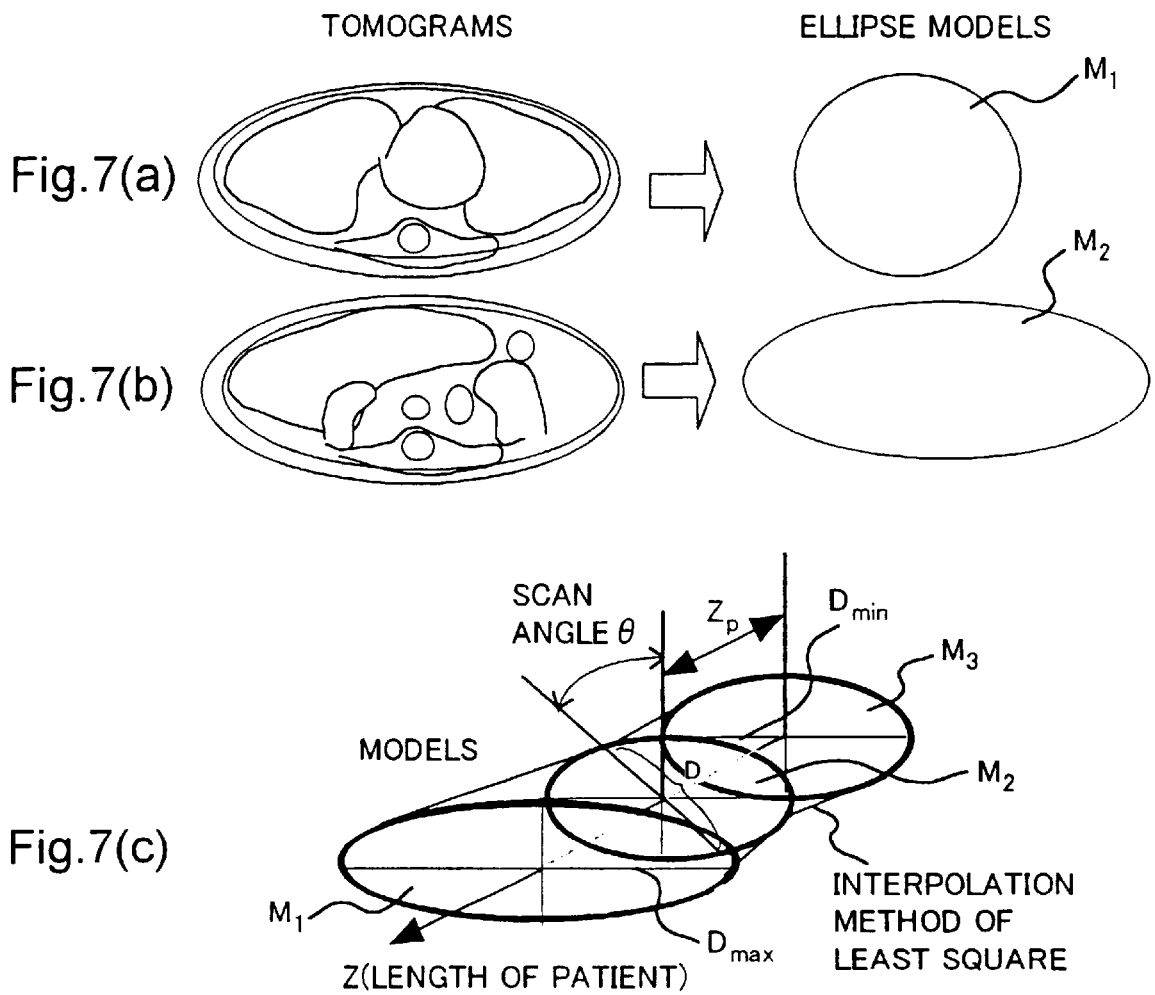

Fig.10(b) MAXIMUM ATTENUATION AMOUNT CHART

X-RAY CT APPARATUS

BACKGROUND OF THE INVENTION

1. Field of the Invention

The present invention relates generally to an X-ray computed tomography (CT) apparatus, and more particularly to an X-ray CT apparatus that reduces the X-ray dose applied to a patient.

2. Description of Related Art

In a conventional X-ray CT apparatus, an X-ray tube current supplied to an X-ray source is controlled according to a part of the body of a patient so that an appropriate X-ray dose is applied to the patient.

Japanese Patent Application Laid-open No. 5-305077 discloses a method in which a control pattern for an X-ray tube current at slice locations is determined in advance according to scannograms obtained in two directions. However, the acquisition of the scannograms in the two directions raises the X-ray dose applied to the patient.

U.S. Pat. No. 5,867,555 discloses a method in which an X-ray tube current is controlled according to transmission data that was stored during a last half rotation of a scanner. However, the X-ray tube current is not appropriate when the intervals of the slices are long. In addition, this method is not suitable for some parts of the body of the patient where the characteristics change considerably, such as before and behind the diaphragm.

SUMMARY OF THE INVENTION

In view of the forgoing, it is an object of the present invention to provide an X-ray CT apparatus that can raise the signal-to-noise ratio and lower the X-ray dose applied to a patient.

To achieve the above-mentioned object, the present invention is directed to an X-ray CT apparatus, comprising: a first device that produces a two-dimensional model that shows transmission lengths of a patient at rotation angles of an X-ray source from scannogram data obtained by a scannography in a single direction for the patient; a second device that sets X-ray tube currents at the rotation angles of the X-ray source according to the two-dimensional model; a third device that performs a CT scan for the patient by applying the X-ray tube currents to the X-ray source; and a fourth device that reconstructs an image from projection data obtained by the CT scan.

The two-dimensional model is preferably an ellipse.

To achieve the above-mentioned object, the present invention is also directed to an X-ray CT apparatus, comprising: a first device that produces a three-dimensional model that shows transmission lengths of a patient at rotation angles of an X-ray source at slice locations of the patient from scannogram data obtained by a scannography in a single direction at the slice locations of the patient; a second device that sets X-ray tube currents at the rotation angles of the X-ray source at the slice locations according to the three-dimensional model; a third device that performs a CT scan for the patient by applying the X-ray tube currents to the X-ray source; and a fourth device that reconstructs images from projection data obtained by the CT scan.

Preferably, the first device produces a two-dimensional ellipse model at each slice location to produce the three-dimensional model.

To achieve the above-mentioned object, the present invention is also directed to an X-ray CT apparatus, comprising: a first device that produces a three-dimensional model that shows transmission lengths of a patient at rotation angles of an X-ray source at slice locations of the patient from CT projection data obtained by a preliminary helical scanning for the patient with a first X-ray dose; a second device that sets X-ray tube currents at the rotation angles of the X-ray source at the slice locations according to the three-dimensional model; a third device that performs a main helical scanning for the patient with a second X-ray dose that is higher than the first X-ray dose by applying the X-ray tube currents to the X-ray source; and a fourth device that reconstructs images from projection data obtained by the main helical scanning.

Preferably, the model is homogenous and its material is similar to that of the patient's body, and transmission lengths of the model are converted into those of the patient.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein:

FIGS. 3(a), 3(b) and 3(c) are explanation drawings showing projections (0°,90°);

FIGS. 4(a), 4(b) and 4(c) are explanation drawings showing difference of projection data at different positions of a patient;

FIGS. 7(a), 7(b) and 7(c) are explanation drawings showing correspondence between slice locations and models;

FIGS. 10(a) and 10(b) are explanation drawings showing a model of the second embodiment.

DETAILED DESCRIPTION OF THE PREFERRED EMBODIMENT

The invention will be described in further detail by way of example with reference to the accompanying drawings.

Figure 1:
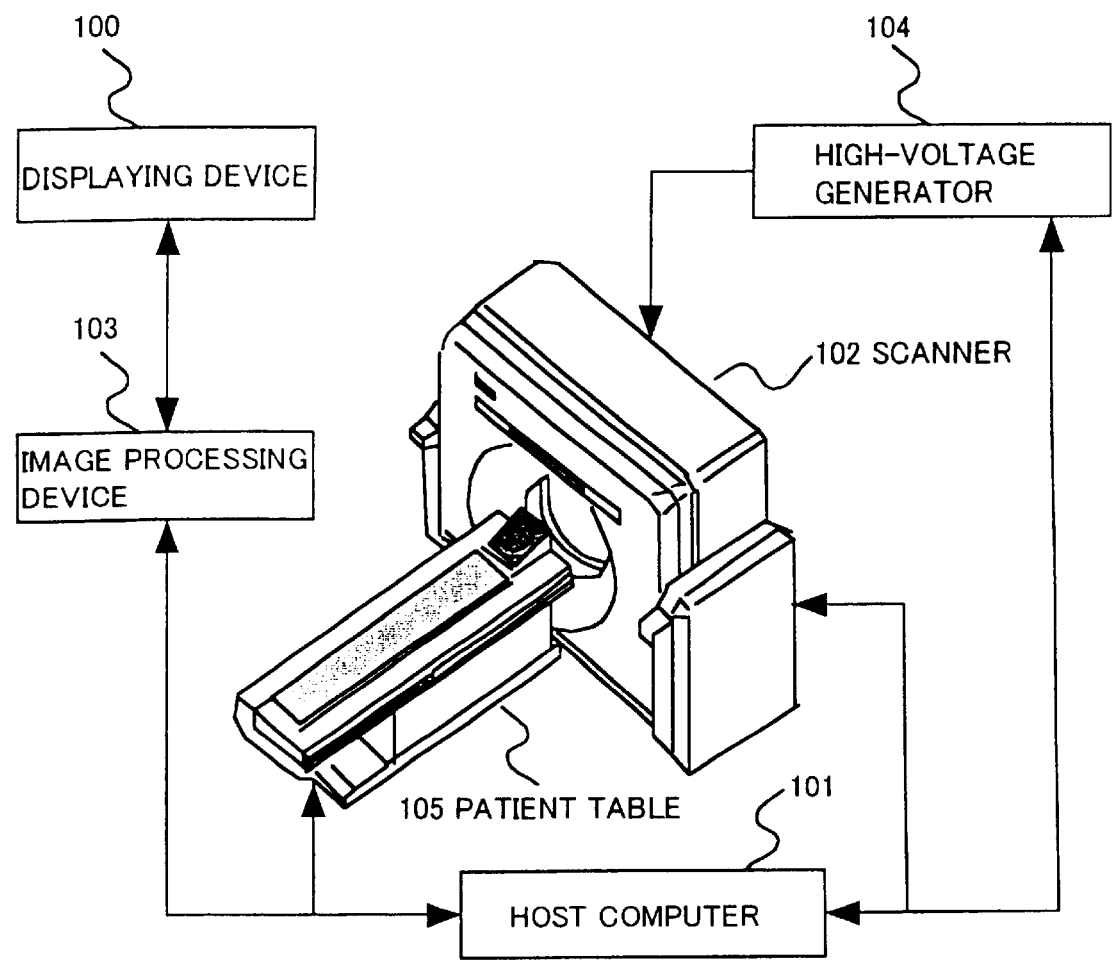
FIG. 1 is a block diagram showing the structure of an X-ray CT apparatus according to the present invention.

FIG. 1 is a block diagram showing the structure of an X-ray CT apparatus according to the present invention. The X-ray CT apparatus comprises a display device 100, a host computer 101 that controls the entire apparatus, a scanner 102 that has an X-ray source 200, X-ray detectors 250, etc. and rotates with respect to a patient, an image processing device 103 that performs image preprocessing, image reconstruction processing and various analytic processings, a high-voltage generator 104 that applies a high voltage to the X-ray source 200, and a patient table 105 on which the patient 202 is placed. The scanner 102 relatively rotates with respect to the patient 202; and the patient 202 is fixed and the scanner 102 rotates, or the scanner 102 is fixed and the patient 202 rotates.

Figure 2:
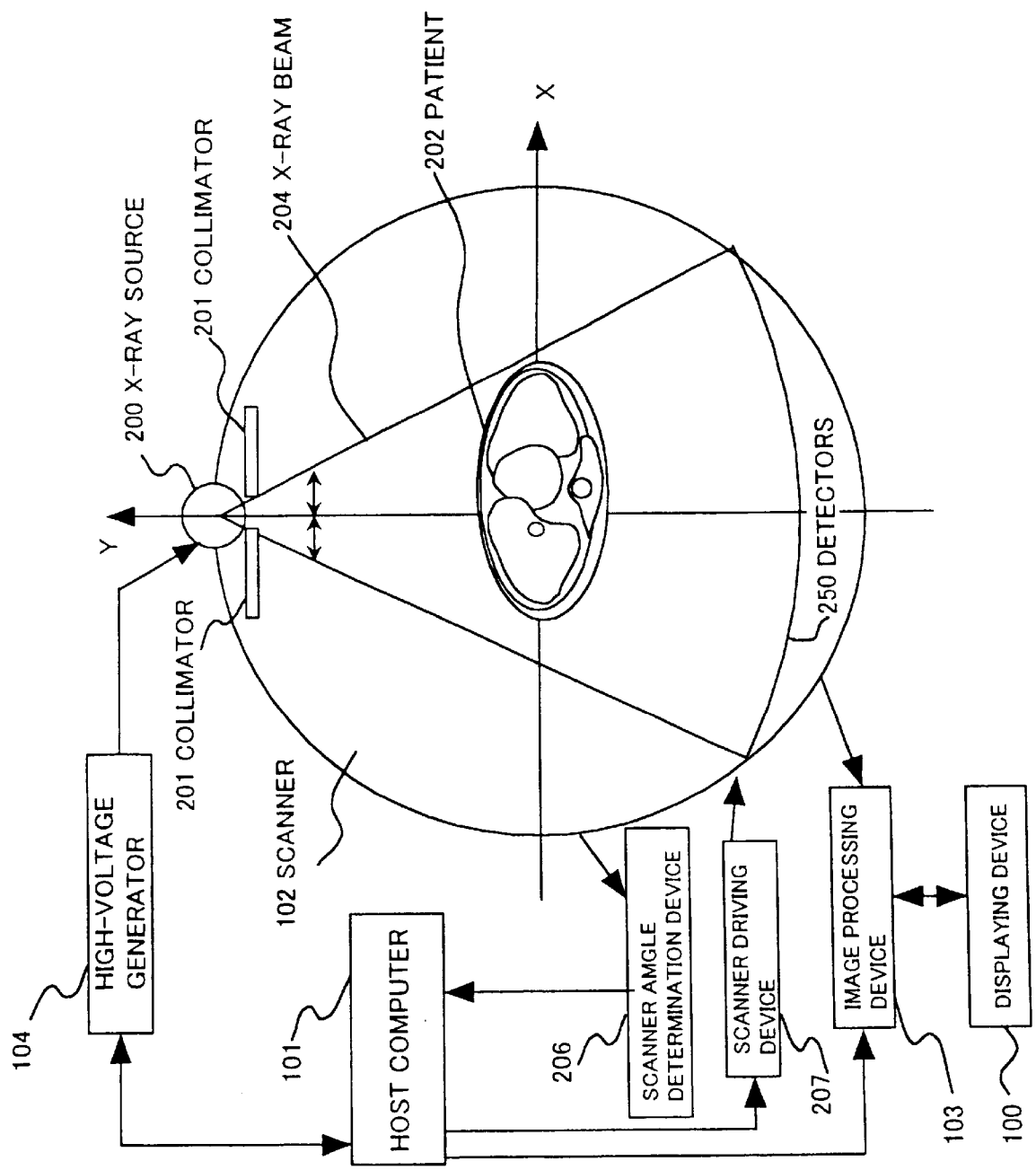
FIG. 2 is a block diagram showing the structure of the X-ray CT apparatus in FIG. 1.

FIG. 2 shows the structure of the scanner 102. The X-ray source 200 and the X-ray detectors 250 face with each other.

A beam of X-rays 204 projected from the X-ray source 200 and collimated by collimators 201 is applied to the patient 202. The X-ray source 200 is controlled by the host computer 101 through the high-voltage generator 104. A scanner angle determination device 206 determines a rotation angle of the scanner 102, and the host computer 101 controls a scanner driving device 207 to drive the scanner 102 according to the determined angle. Data acquired by the detectors 250 is matched with the data on the angles and so on stored in the host computer 101 at the image processing device 103, and a reconstructed image is displayed on the displaying device 100.

In the first embodiment of the present invention, a scannogram is taken in a single direction to obtain a standard model before the CT scan, and an X-ray tube current supplied to the X-ray source 200 is controlled according to the standard model at the CT scan. The standard model is made from a material that is close to that of the patient, and an X-ray transmission length of the patient can be calculated for each rotation angle of the scanner from the model that shows a relation between the rotation angle of the scanner and the transmission length. After the model is obtained, the main CT scan is performed with the model. Transmission length is found for each rotation angle of the scanner from the model, and an X-ray tube current corresponding to each transmission length is calculated, and the X-ray tube current is controlled at each rotation angle. Each interval of the rotation angles is one basic pitch or some pitches.

In case of a single-position scanning in which the patient is not moved, the model is a single model (a two-dimensional model with two axes of the rotation angle of the scanner and the transmission length) at the single position. In case of a helical scanning in which the patient is moved along its length, a two-dimensional model (a two-dimensional model at each position Z with two axes of the rotation angle of the scanner and the transmission length) at each position along the helical scanning direction (length of the patient) is needed. In the latter case, if the number of the models is small (the intervals of the positions are long), one or more models at positions between two adjacent positions are interpolated to construct a three-dimensional model.

The two-dimensional model is, for example, an ellipse with a minor axis and a major axis. The lengths of the minor axis and the major axis change according to the transmission lengths at each position. The model is homogenous and its material is similar to that of the patient's body. This is preferably water or the like, but it may be other material. A coefficient of the material (material coefficient) is found in advance, and the lengths of the minor axis and the major axis are calculated or the X-ray tube current is calculated with the material coefficient.

The above idea will now be more specifically explained.

First, the premises for the present invention will be explained. FIGS. 3(a), 3(b) and 3(c) show the relation between the rotation angle of the scanner and projection data. The patient is placed so that the patient's center is substantially the same as the isocenter that is the center of the rotation of the scanner. When the angle of the scanner (the X-ray source) is 0°, the X-ray passes the minor axis of the patient (the shortest path). When the angle of the X-ray source is 90°, the X-ray passes the major axis of the patient (the longest path).

The projection data in FIGS. 3(b) and 3(c) shows the attenuation amounts of the X-rays from the amounts of X-rays determined by the X-ray detectors. The x-axis shows the width of the patient, and the y-axis shows the attenuation amounts of the X-rays that correspond to the lengths of the paths the X-rays have passed. The width of the patient at the isocenter can be calculated from expanse of the projection data along the channel direction. The number of data channels concerning the patient is multiplied by a channel interval of the detectors, and the product is divided by a distance SOD between the X-ray source and the X-ray detectors, and the quotient is multiplied by a distance SID between the X-ray source and the isocenter. The result of this calculation is the width of the patient at the isocenter.

The difference between absorption rates of the projection data will be explained with reference to FIGS. 4(a), 4(b) and 4(c). The density of the patient is not even since the patient has lungs, bones, etc. For example, the attenuation amounts (FIG. 4(c)) of the X-rays that have passed a lung are smaller than the attenuation amounts (FIG. 4(b)) of the X-rays that have passed a lever, though the lengths of the paths are the same. The attenuation amounts of the X-rays vary from path to path according to the parts the X-rays have passed even if the lengths of the paths are the same.

A certain amount of transmission X-rays is needed to reconstruct a tomogram, but too much X-ray beam is of no use and it just raises the X-ray dose applied to the patient.

The calculation of the models will be explained next.

Before the CT scan, the scannogram is taken for the patient along a single direction to obtain scannogram image data. The X-ray tube current at this time is, for example, 10 mA or lower.

Figures 5A, 5B, 5C:
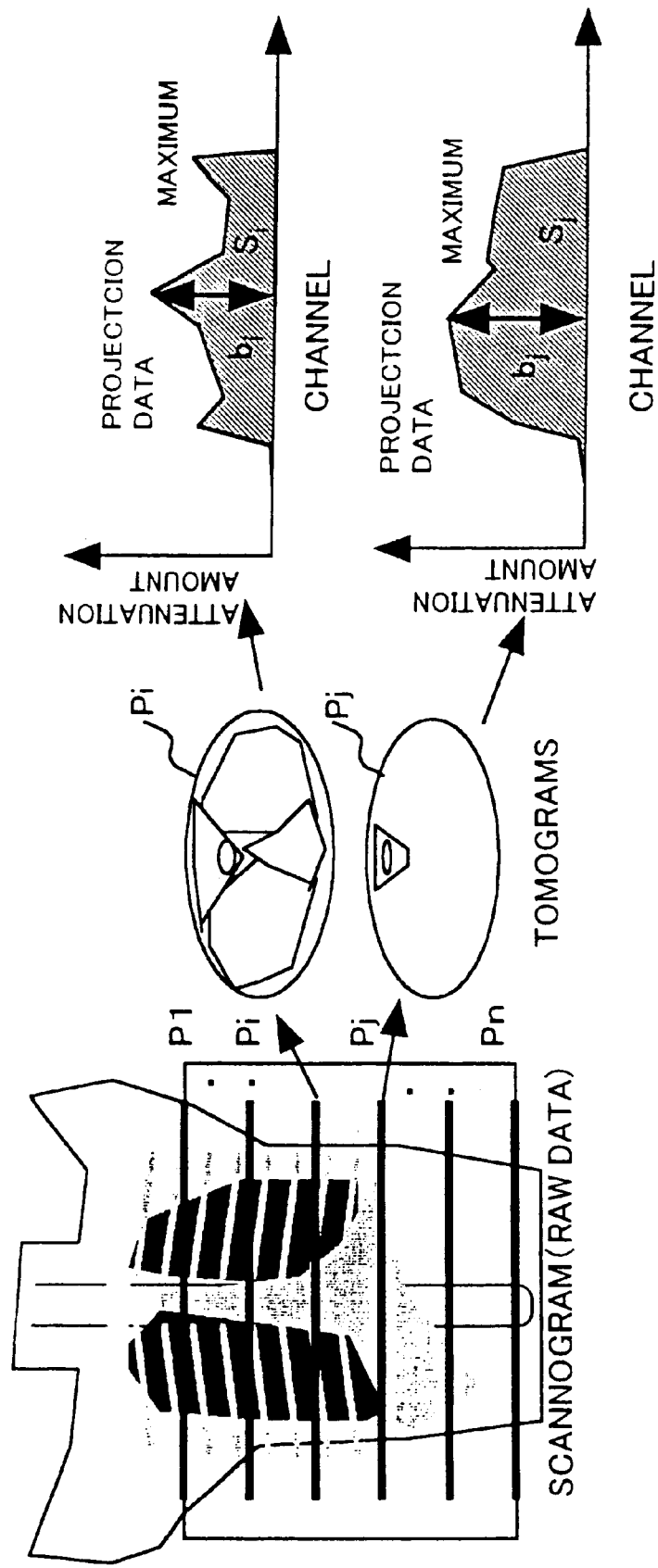
FIGS. 5(a), 5(b) and 5(c) are explanation drawings showing scannograms and projection data.

FIG. 5(a) shows a scannogram 300 taken from the abdomen to the back within the part between the chest and the middle of the abdomen. Slice locations $P_1, \ldots, P_i, \ldots, P_j, \ldots, P_n$ in FIG. 5(a) are determined within the range.

FIGS. 5(b) and 5(c) are explanatory diagrams showing the production of the models. FIG. 5(b) shows the CT images at the slice locations $P_i$ and $P_j$ (they are examples and are not related to each other), and FIG. 5(c) shows the projections of the vertical attenuation amounts. The maximum attenuation amount $b_i$ and the projection area $S_i$ reflect the transmission state at the slice location $P_i$, and the maximum attenuation amount $b_j$ and the projection area $S_j$ reflect the transmission state at the slice location $P_j$.

Let the models be ellipses, and the areas $S_i$ and $S_j$ of the ellipses are shown by the following equations 1;

$$S_i = (\pi \cdot a_i \cdot b_i)/4,$$

and $$S_j = (\pi \cdot a_j \cdot b_j)/4, \quad \text{equations 1}$$

where the lengths of the minor axes are $b_i$ and $b_j$ and the lengths of the major axes are $a_i$ and $a_j$.

When the areas $S_i$ and $S_j$ and the lengths of the minor axes $b_i$ and $b_j$ are known, the lengths of the major axes $a_i$ and $a_j$ are shown by the following equations 2;

$$a_i = 4S_i/(\pi \cdot b_i),$$

and $$a_j = 4S_j/(\pi \cdot b_j). \quad \text{equations 2}$$

Actually, the areas $S_i$ and $S_j$ and the lengths of the minor axes $b_i$ and $b_j$ of the ellipse models need to be corrected according to the material. The material coefficient k is used to determine the transmission lengths according to the material. The material coefficient may be set for each of the length of the minor axis b and the area S, but it is set for only the length of the minor axis b in the embodiment, $b_{i1}=kb_i$ is substituted for $b_i$ in equations 2 and $b_{j1}=kb_j$ is substituted for $b_j$ in equations 2 to form equations 3;

$$a_i=4S_i/(\pi \cdot b_{i1})=4S_i/(\pi \cdot kb_i),$$

and $$a_j=4S_j/(\pi \cdot b_{j1})=4S_j/(\pi \cdot kb_j). \qquad \text{equations 3}$$

The material is, for example, water, and it may be polyethylene or acrylic resin.

Figure 6A:
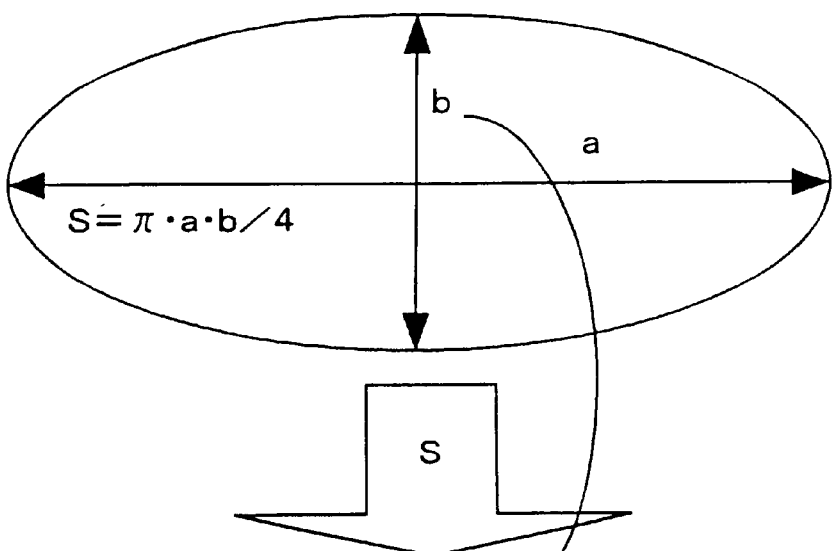
FIGS. 6(a) and 6(b) are explanation drawings showing models.
Figure 6B:
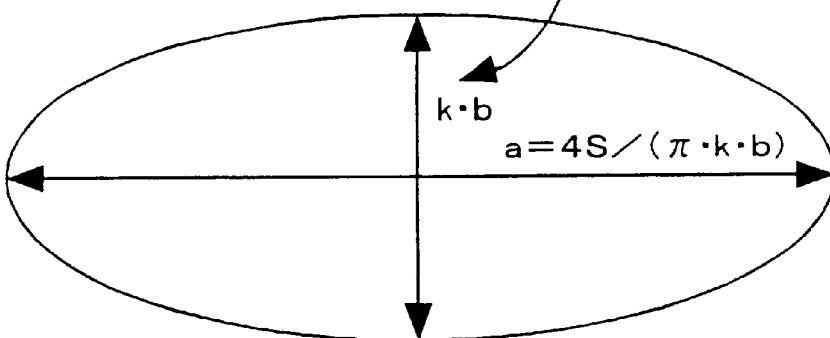

FIG. 6(a) shows an ellipse model produced from the scannogram, and FIG. 6(b) shows an ellipse model that reflects the material coefficient k.

FIGS. 7(a) and 7(b) show tomographic images and corresponding ellipse models $M_1$, and $M_2$, respectively. The model $M_1$ is a circle whose minor axis is as long as the major axis (a=b), and the model $M_2$ is an ellipse whose major axis is twice as long as the minor axis (a=2b). FIG. 7(c) shows a plurality of models $M_1$, $M_2$ and $M_3$ along the length of the patient. If the intervals $Z_P$ between the models $M_1$, $M_2$ and $M_3$ are long, one or more models are interpolated between adjacent positions in the method of least square.

The method of finding the X-ray tube current will be explained next.

As shown in FIGS. 5(b), 7(a) and 7(b), the models reflect the transmission lengths of the tomographic images at the slice locations. The models are temporarily stored in a memory storing a resister. If the models are produced and to be used, the register is used. After a slice location is determined, the model at the position is read from the memory and the X-ray tube current is determined for each scanner angle according to the transmission length obtained from the model. Then, the X-ray tube current is controlled at each scanner angle.

Figure 8:
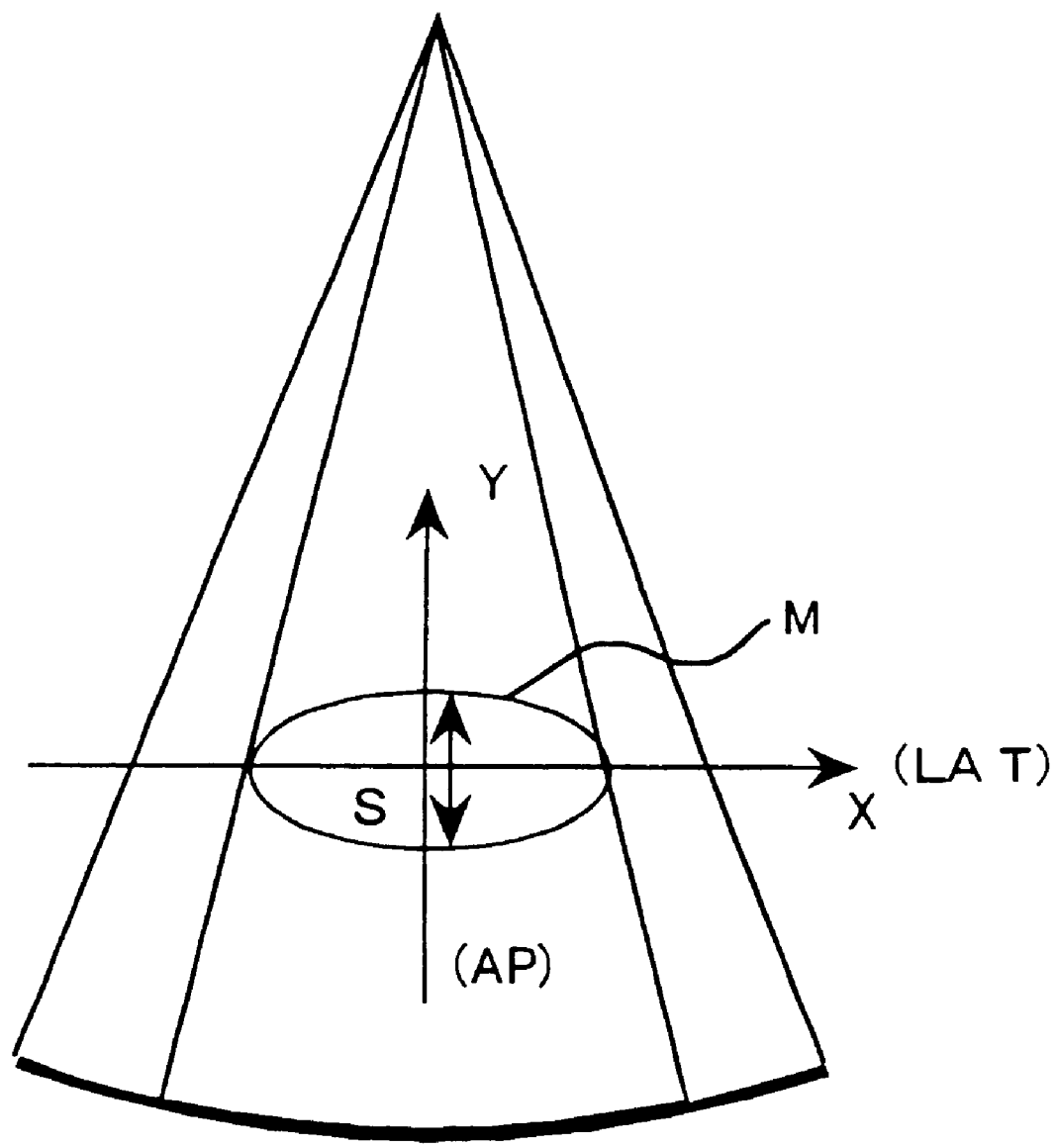
FIG. 8 is an explanation drawing showing a relation between a model and projection.

The X-ray tube currents will be explained with reference to FIGS. 7(c) and 8. FIG. 7(c) shows a state in which the rotation angle β of the scanner with respect to the model M is 0°. Suppose the model M is produced from the scannogram at the rotation angle of 0°. When a path is inclined by a rotation angle θ at the CT scan with respect to the model M, the length D of the path that includes the center of the ellipse model M (for example, the isocenter) is shown by the following equation 4 (see FIG. 7(c));

$$D=(a \cdot kb)/\sqrt{(kb)^2 \cdot \sin^2\theta + a^2 \cos^{2\theta}}, \qquad \text{equation 4}$$

where a indicates $a_i$ or $a_j$ in equations 3.

Let the maximum of the lengths of the paths (at all the slice locations) of the whole scanning part be $D_{max}$, and let the minimum of them be $D_{min}$. The maximum and the minimum are known when the models are produced. When the X-ray tube current is changed within the range between $I_{min}$ (mA) and $I_{max}$ (mA), the X-ray tube current I at the path D is shown by the following equation 5, $$I=\{D \cdot (I_{max}-I_{min})\}/(D_{max}-D_{min}). \qquad \text{equation 5}$$

The X-ray tube current I is found for each rotation angle θ of the scanner by the equations 4 and 5. The X-ray tube current is controlled at each rotation angel θ. At the CT scan, the X-ray source is controlled with the X-ray tube current I determined by the model M at each rotation angle of the scanner, and thus the appropriate amounts of X-rays are applied according to the lengths of the paths.

As described above, in the first embodiment, the scannogram is taken in only one direction to produce the models. This reduces the X-ray dose applied to the patient, compared with the conventional method in which the scannograms are taken in two directions.

The second embodiment of the present invention will now be explained. In the second embodiment, a preliminary radiography, for example, a CT scan (real-time CT radioscopy) with a small amount of X-rays is performed to produce a model before the main radiography (the CT scan).

A helical scanning as the preliminary radiography will now be explained. The X-ray tube current I at the preliminary radiography is, for example, 20 mA (the X-ray tube current at the main radiography is, for example, 100 to 200 mA).

Figure 9:
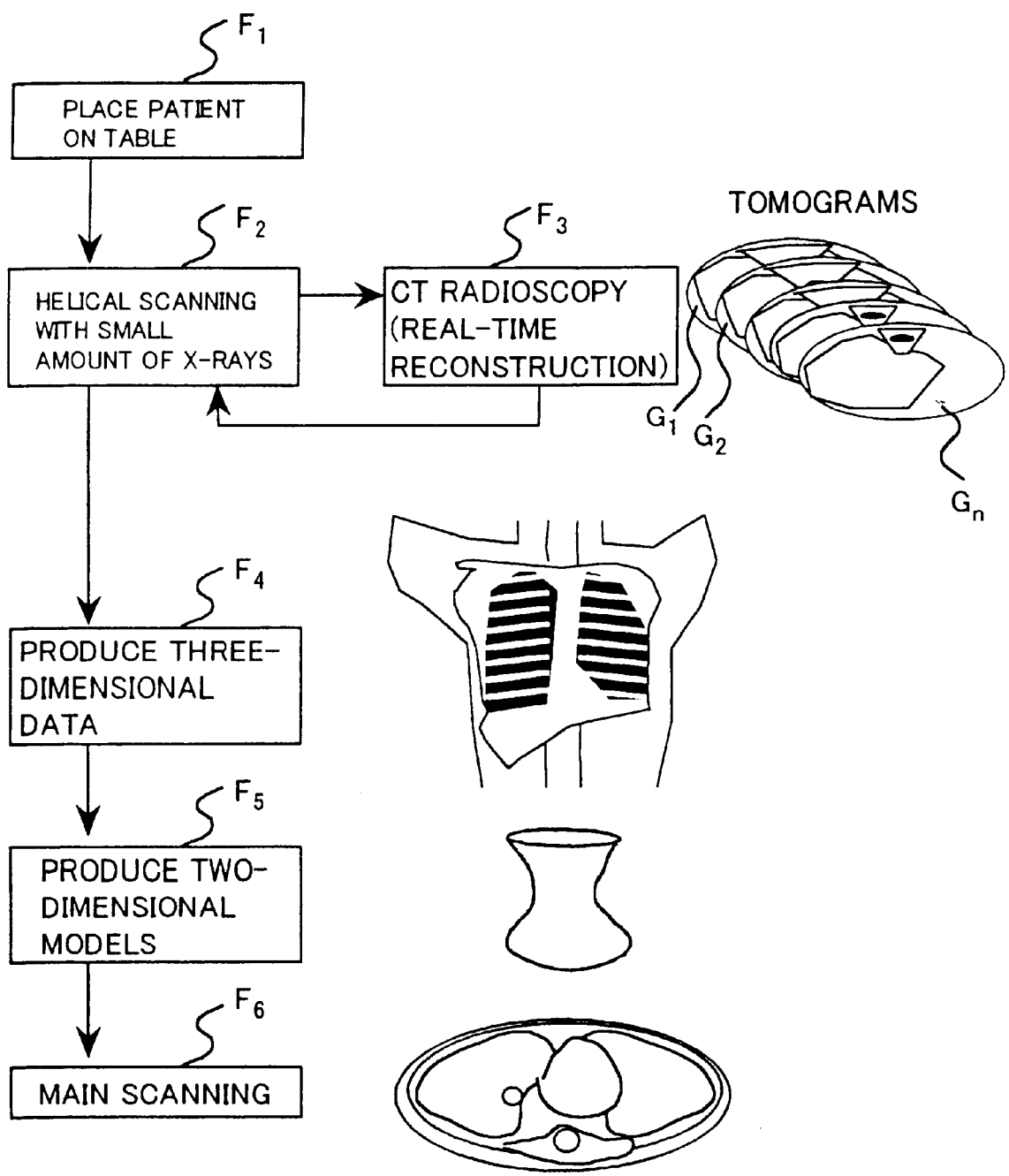
FIG. 9 is a flowchart showing a processing of a second embodiment.

FIG. 9 is a flowchart showing a procedure of the measurement, the processing and the control. The patient is placed on the bed at step $F_1$, and the preliminary helical scanning is performed at step $F_2$. The part for the preliminary scanning along the length of the patient is preferably the same as that for the main scanning, but they may be different (for example, the part for the preliminary scanning is smaller than that for the main scanning).

Then, at step $F_3$, the CT radioscopy (the real-time reconstruction) is performed according to the projection data obtained at step $F_2$ to acquire reconstructed image data $G_1$, $G_2$, ..., $G_n$ at a plurality of slice locations. For example, the length of the radioscopy part is 300 mm and the intervals between the slice locations are 1mm, the reconstructed image data at 300 slice locations is acquired. Scannogram data along any direction is obtained from each of the 300 reconstructed images at step $F_4$. Then, the sections of the patient are approximated to ellipses according to the scannogram data to produce 300 two-dimensional models (a three-dimensional image) at step $F_5$. After that, an ordinary CT scan or a helical scanning is performed as the main scanning at step $F_6$. In case of the ordinary CT scan, the CT scan is performed at one slice location, and the model at the position is selected. The X-ray tube current is controlled at each rotation angle of the scanner to apply the appropriate amount of X-rays. In case of the helical scanning, the X-ray tube current is controlled at each rotation angle of the scanner at the slice locations with intervals of 1 mm in order to apply the appropriate amount of X-rays. In this case, the X-ray beam is continuously applied, and the amounts of the X-rays at positions between the slice locations is a question. For example, each model is used until the next model is used, or models are interpolated between the models in a method, for example, the method of least square.

Though the number of the reconstructed images at step $F_4$ is 300, reconstructed images may be interpolated at the step for producing more models at step $F_5$.

Figure 10A:
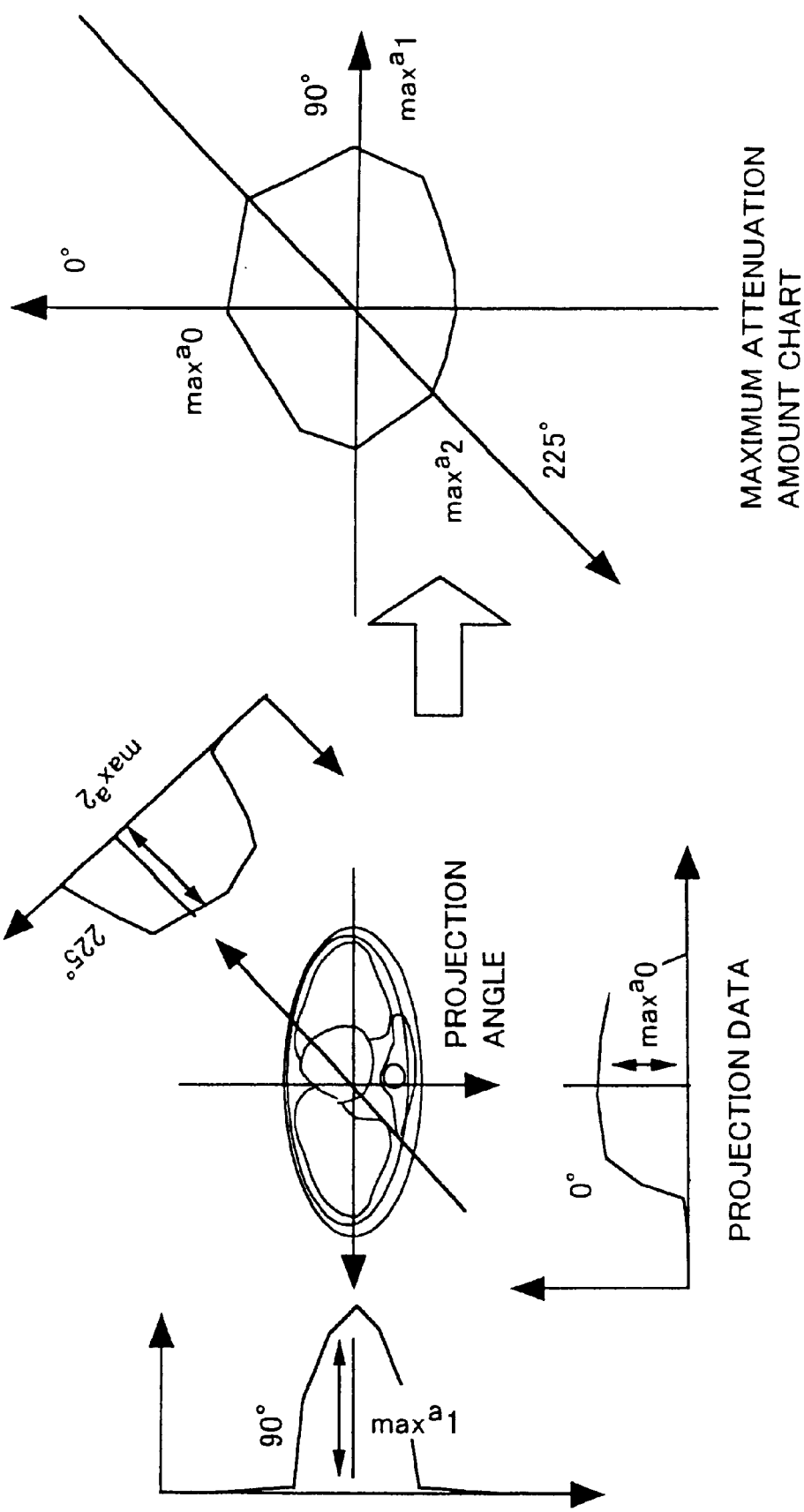

The sections of the patient are approximated to the ellipses according to the scannogram data to produce the models in the same way as in the first embodiment. A method of producing models with a higher reality by making the most of the characteristics of the reconstructed images will be explained. The helical scanning at step $F_2$ corresponds to scannographies at angles between 0° and 360°. The scannograms are obtained at projection angles between 0° and 360°. If the intervals of the projection angles are 0°, the projection is continuous. If it is θ° other than 0°, the projections are performed at the projection angles with the intervals of θ°. Any angles can be set as the intervals θ°. FIGS. 10(a) and 10(b) are diagrams showing the state in which the intervals θ° are 45°.

The projections are performed at the projection angles 0° (180°), 45° (225°), 90° (270°) and 135° (315°) as shown in FIG. 10(a), and the maximums $a_1$, $a_2$, $a_3$ and $a_4$ of the attenuation amounts are found. FIG. 10(b) is a chart showing the maximums. Though it is a polygonal line chart, it is a model that is more real than that of the first embodiment. The smaller the intervals θ° are, the higher the reality is.

In the second embodiment, since the helical scanning is performed as the preliminary radiography, the X-ray dose applied to the patient at the preliminary radiography is a little higher than that of the conventional method in which scannographies are performed in two directions as the preliminary radiography. However, since the model of the second embodiment is far more real than that of the conventional method, the X-ray dose applied to the patient at the main radiography can be quite minimized. Thus, the X-ray dose applied to the patient in total through the preliminary radiography and the main radiography can be lowered compared with the conventional method.

If energy is fixed, the attenuation amount of the X-ray is in proportion to the transmission length of the material. If the material is water that is close to that of the patient, FIG. 10(b) shows the thicknesses of the patient at the projection angles.

A relation between the raw data (scannogram data) obtained by the CT detectors and a water equivalent length (water transmission length). The water equivalent length is a thickness converted to for water from that for an unknown material. The thickness converted to for polyethylene is called the polyethylene equivalent length.

Let a raw data value be $b_0$. The value $b_0$ is a positive number, for example, 0 to 30000 (the maximum varies from apparatus to apparatus). The CT value of water is 0. Let a linear attenuation coefficient of water with respect for energy E of a photon be $\mu_w(E)$.

Since a CT value $CT_0(E)$ of an object A is shown by the following equation 6 from the definition of a CT value, $$CT_0(E) = \{1000 \cdot (\mu_0(E) - \mu_W(E))\}/\mu_W(E), \quad \text{equation 6}$$

where $\mu_0(E)$ is a linear attenuation coefficient of the object A; the linear attenuation coefficient $\mu_0(E)$ is shown by the following equation 7, $$\mu_0(E) = \{\mu_W(E) \cdot (CT_0(E) + 1000)\}/1000. \quad \text{equation 7}$$

A transmission ratio $D_a(t_0, E)$ of the X-ray with the energy E through the object A with a thickness $t_0$ is shown by the following equation 8, $$D_a(t_0, E) = \exp(-\mu_0(E) \cdot t_0). \quad \text{equation 8}$$

The overall transmission ratio $D_a(t_0)$ of the X-rays is an integration of the transmission ratio $D_a(t_0, E)$ over all the energies as shown by the following equation 9, $$D_a(t_0) = \int D_a(t_0, E) dE / \int dE. \quad \text{equation 9}$$

Suppose that an energy $E_e$ approximately satisfies the following equation 10, $$\exp(-\mu_0(E_e)) = \int \exp(-\mu_0(E)) dE / \int dE, \quad \text{equation 10}$$

then the following equation 11 is formed, $$D_a(t_0) = \exp(-\mu_0(E_e) \cdot t_0). \quad \text{equation 11}$$

Linear attenuation coefficients $\mu_e$ and $\mu_{we}$ are shown in the following equations 12, $$\mu_e = \mu_0(E_e),$$

and $$\mu_{we} = \mu_W(E_e). \quad \text{equation 12}$$

Since the transmission ratio $D_a(t_0)$ is transformed into logarithm and the sign of the logarithm is changed to find a value of the raw data; the value $D_S(t_0)$ is shown by the following equation 13, $$D_S(t_0) = -\log(D_a(t_0)) = \mu_e \cdot t_0 = \{t_0 \cdot \mu_{we} \cdot (CT_0 + 1000)\}/1000. \quad \text{equation 13}$$

A thickness $t_W$ of water for acquiring the same value is equivalent to the thickness to of the object A. The thickness $t_W$ is the water equivalent length, and the following equation 14 is formed, $$D_S(t_0) = t_W \cdot \mu_{we} \quad \text{equation 14}.$$

Thus, the water equivalent length $t_W$ is shown by the following equation 15, $$t_W = \{t_0 \cdot (CT_0 + 1000)\}/1000 \quad \text{equation 15}.$$

Suppose the value of the data for the object A (CT value $CT_0$ and thickness $t_0$) is shown by the following equation 16, $$D_S(t_0) = b_0 \quad \text{equation 16};$$

then the following equation 17 is formed, $$\mu_{we} = b_0/t_W = \{(b_0/t_0) \cdot (1000)\}/(CT_0 + 1000) \quad \text{equation 17}.$$

Thus, a water equivalent length $t_{WX}$ for a data value $b_X$ can be found from known values as shown by the following equation 18, $$t_{WX} = \{b_X \cdot (t_0/b_0) \cdot (CT_0 + 1000)\}/1000 \quad \text{equation 18}.$$

In case of water, the CT value $CT_0$ is 0. In case of polyethylene, when the data value $b_0$ for a polyethylene phantom (CT value $CT_0$ is 150 and thickness $t_0$ is 310 mm) is known to be 9000, the water equivalent length $t_W$ that is equivalent to the thickness $t_0$ is 356.5 mm. When the data value $b_X$ for polyethylene with an unknown thickness is 5806, the water equivalent length $t_{WX}$ can be found to be 230 mm.

In the first embodiment, the host computer 101 instructs the scanner driving device 207 to take the scannogram, produces the models, calculates the X-ray tube currents at the rotation angles of the scanner, and instructs the high-voltage generator 104 to control the X-ray tube currents in accordance with operation by the operator. In the second embodiment, the host computer 101 instructs the scanner driving device 207 to perform the preliminary helical scanning, produces the models, calculates the X-ray tube currents at the projection angles, and instructs the high-voltage generator 104 to control the X-ray tube currents in accordance with operation by the operator. The host computer 101 can work with the image processing device 103.

In the first and second embodiments, the maximums of the data values are determined at the model production, but the maximums can be affected by high-frequency noises and so on. To eliminate the noises, the signals pass through a filter, or the signals are smoothed or averaged.

In the embodiments, the scanner including the X-ray source and the X-ray detectors is rotated. However, in case of an apparatus with detectors arranged around the patient, only the X-ray source rotates.

According to the present invention, the amounts of X-rays transmitted through the patient are appropriately controlled in order to raise the signal-to-noise ratio and lower the X-ray dose applied to the patient.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A CT scanning method comprising:
   using preliminary X-ray data obtained by scanning a patient with X-rays to create a mathematical model of at least a part of the patient's body;
   said mathematical model describing shapes of X-ray attenuating material for respective linear displacements between an X-ray source and the patient, where said attenuating material is homogeneous within each of at least some of the shapes, at least some of the shapes are non-circular, and the shapes differ from each other for at least some different relative linear displacements between the X-ray source and the patient;
   carrying out imaging CT scanning of at least a part of the patient's body by using the mathematical model to estimate and control properties of an X-ray beam used in said imaging CT scanning in accordance with a positional relationship between the X-ray beam and said shapes and information related to said X-ray attenuating material;
   deriving imaging X-ray data from said scanning; and
   reconstructing X-ray images from said imaging X-ray data.

2. A method as in claim 1 comprising carrying out a preliminary CT scan of at least a part of the patient's body, at a number of relative angular and linear displacements between the X-ray source and the patient, and at an average X-ray dosage to the patient much lower than an average dosage for said imaging CT scanning, to derive said preliminary X-ray data.

3. A method as in claim 2 wherein at least some of said shapes are polygonal.

4. A method as in claim 2 in which the number of said angular positions in said preliminary CT scan is greater than two but much less than a number of angular positions used in said imaging CT scanning.

5. A method as in claim 2 in which said preliminary scan is a helical CT scan.

6. A method as in claim 2 wherein at least some of said shapes are elliptical.

7. A method as in claim 1 comprising carrying out a scan at only a single angle between the X-ray source and the patient to derive said preliminary X-ray data.

8. A method as in claim 1 wherein at least some of said shapes are elliptical.

9. A method as in claim 1 in which said using the mathematical model to estimate and control properties of the X-ray beam comprises converting attenuation values for paths through said shapes to X-ray transmission path lengths for respective paths through the patient.

10. A CT scanning system comprising:
    a first scanning and data processing system carrying out a preliminary scan of a patient to derive preliminary X-ray data and processing the preliminary X-ray data to create a mathematical model of at least a part of the patient's body;
    said mathematical model describing shapes of X-ray attenuating material for respective linear displacements between an X-ray source and the patient, where said attenuating material is homogeneous within each of at least some of the shapes, at least some of the shapes are non-circular, and the shapes differ from each other for at least some different relative linear displacements between the X-ray source and the patient;
    a second scanning and data processing system carrying out imaging CT scanning of at least a part of the patient's body by using the mathematical model to estimate and control properties of an X-ray beam used in said imaging CT scanning in accordance with a positional relationship between the X-ray beam and said shapes and information related to said X-ray attenuating material;
    said second scanning system deriving imaging X-ray data from said imaging scanning and reconstructing X-ray images from said imaging X-ray data.

11. A system as in claim 10 in which said first scanning and data processing system scans the patient at a lower average X-ray dosage to the patient than said second scanning and data processing system.

12. A system as in claim 10 in which said first and second scanning and data processing systems comprises an X-ray source and derive said preliminary X-ray data for more than angular positions of the X-ray source that are more than two but are substantially fewer than a number of angular positions for which said imaging data is derived.

13. A system as in claim 10 in which said first scanning and data processing system carries out a helical CT scan.

14. A system as in claim 10 in which said first scanning and data processing system comprises an X-ray source and derives said preliminary X-ray data at only a single angular position of the X-ray source.

15. A system as in claim 10 in which at least some of said shapes are elliptical.

16. A system as in claim 10 in which said second scanning and data processing system uses the mathematical model to estimate and control properties of the X-ray beam in a process comprising converting attenuation values for paths through said shapes to X-ray transmission path lengths for respective paths through the patient.

17. An X-ray CT apparatus, comprising:
    a first device that produces a two-dimensional model that shows transmission lengths of a patient at rotation angles of an X-ray source from scannogram data obtained by a scannography in a single direction for the patient;
    a second device that sets X-ray tube currents at the rotation angles of the X-ray source according to the two-dimensional model;
    a third device that performs a CT scan for the patient by applying the X-ray tube currents to the X-ray source; and
    a fourth device that reconstructs an image from projection data obtained by the CT scan.

18. The X-ray CT apparatus as defined in claim 17, wherein the two-dimensional model is an ellipse.

19. The X-ray CT apparatus as defined in claim 17 wherein:
    the two-dimensional model is homogenous and its material is similar to that of the patient's body; and
    transmission lengths of the two-dimensional model are converted into those of the patient.

20. An X-ray CT apparatus, comprising:
    a first device that produces a three-dimensional model that shows transmission lengths of a patient at rotation angles of an X-ray source at slice locations of the patient from scannogram data obtained by a scannography in a single direction at the slice locations of the patient;

a second device that sets X-ray tube currents at the rotation angles of the X-ray source at the slice locations according to the three-dimensional model;

a third device that performs a CT scan for the patient by applying the X-ray tube currents to the X-ray source; and a fourth device that reconstructs images from projection data obtained by the CT scan.

21. The X-ray CT apparatus as defined in claim 20, wherein the first device produces a two-dimensional ellipse model at each slice location to produce the three-dimensional model.

22. The X-ray CT apparatus as defined in claim 20, wherein:

the three-dimensional model is homogenous and its material is similar to that of the patient's body; and transmission lengths of the three-dimensional model are converted into those of the patient.

23. An X-ray CT apparatus, comprising:

a first device that produces a three-dimensional model that shows transmission lengths of a patient at rotation angles of an X-ray source at slice locations of the patient from CT projection data obtained by a preliminary helical scanning for the patient with a first X-ray dose;

a second device that sets X-ray tube currents at the rotation angles of the X-ray source at the slice locations according to the three-dimensional model;

a third device that performs a main helical scanning for the patient with a second X-ray dose that is higher than the first X-ray dose by applying the X-ray tube currents to the X-ray source; and a fourth device that reconstructs images from projection data obtained by the main helical scanning.

24. The X-ray CT apparatus as defined in claim 23, wherein:

the three-dimensional model is homogenous and its material is similar to that of the patient's body; and transmission lengths of the three-dimensional model are converted into those of the patient.

* * * * *